United States Patent
Eddy et al.

(10) Patent No.: US 10,388,143 B2
(45) Date of Patent: Aug. 20, 2019

(54) PATIENT MOVEMENT AND INCONTINENCE NOTIFICATION DEVICES

(71) Applicant: Parasol Medical LLC, Buffalo Grove, IL (US)

(72) Inventors: Patrick E. Eddy, Allendale, MI (US); Michael Kilcran, Antioch, IL (US)

(73) Assignee: Parasol Medical LLC, Buffalo Grove, IL (US)

( * ) Notice: Subject to any disclaimer, the term of this patent is extended or adjusted under 35 U.S.C. 154(b) by 0 days.

(21) Appl. No.: 15/435,767

(22) Filed: Feb. 17, 2017

(65) Prior Publication Data

US 2017/0236398 A1 Aug. 17, 2017

Related U.S. Application Data

(60) Provisional application No. 62/296,201, filed on Feb. 17, 2016.

(51) Int. Cl.
*G08B 21/20* (2006.01)
*A61B 5/11* (2006.01)
(Continued)

(52) U.S. Cl.
CPC ............ *G08B 21/20* (2013.01); *A61B 5/1115* (2013.01); *A61B 5/202* (2013.01); *A61B 5/6808* (2013.01);
(Continued)

(58) Field of Classification Search
CPC .......... A61F 2013/426; A61F 2013/423; A61F 2013/428; A61F 13/42; A61F 2013/424;
(Continued)

(56) References Cited

U.S. PATENT DOCUMENTS 3,954,100 A * 5/1976 Sem-Jacobsen ... A61B 5/04085
600/393
5,144,284 A * 9/1992 Hammett .............. A61B 5/1115
128/886

(Continued)

FOREIGN PATENT DOCUMENTS

| CN | 103617700 A | 3/2014 |
| EA | 018662 | 9/2013 |
| GB | 2501561 A | 10/2013 |

*Primary Examiner* — Orlando Bousono
*Assistant Examiner* — Son M Tang
(74) *Attorney, Agent, or Firm* — Price Heneveld LLP

(57) ABSTRACT

A notification device is provided that includes a sensor pad, and an electronics module generates one or more notifications in response to signals received from the sensor pad. In a first embodiment, the sensor pad includes a pressure sensor for sensing pressure applied by a patient and generating a pressure signal, and conductive tracings for sensing moisture due to incontinence and generating a moisture detection signal when moisture is detected. In another embodiment, an absorbent sensor pad includes a sensor pad for sensing moisture and includes an absorbent chuck having a moisture-impermeable sheet with an absorbent material on an upper surface thereof, wherein the moisture-impermeable sheet has an aperture for receiving the sensor pad. The absorbent sensor pad may be provided in the form of a diaper.

16 Claims, 6 Drawing Sheets

(51) Int. Cl.
*A61B 5/00* (2006.01)
*A61F 13/42* (2006.01)
*G08B 21/04* (2006.01)
*A61B 5/20* (2006.01)
*G08B 21/22* (2006.01)

(52) U.S. Cl.
CPC ............ *A61B 5/6892* (2013.01); *A61F 13/42* (2013.01); *G08B 21/0461* (2013.01); *A61B 5/0022* (2013.01); *A61B 5/6891* (2013.01); *A61B 5/6894* (2013.01); *A61B 5/746* (2013.01); *A61F 2013/424* (2013.01); *G08B 21/22* (2013.01)

(58) Field of Classification Search
CPC .... G08B 21/20; G08B 21/0461; G08B 21/22; A61B 5/1115; A61B 5/202; A61B 5/6808; A61B 5/6892; A61B 5/002; A61B 5/6891; A61B 5/6894; A61B 5/746
See application file for complete search history.

(56) References Cited

U.S. PATENT DOCUMENTS

| | | | | |
|---|---|---|---|---|
| 5,342,583 | A * | 8/1994 | Son | A61F 5/451 2/84 |
| 5,844,488 | A * | 12/1998 | Musick | G08B 21/22 340/573.4 |
| 6,200,250 | B1 * | 3/2001 | Janszen | A61F 13/42 493/334 |
| 6,283,938 | B1 * | 9/2001 | McConnell | A61K 9/0009 604/66 |
| 6,372,951 | B1 * | 4/2002 | Ter-Ovanesyan | A61B 5/04884 600/373 |
| 6,384,296 | B1 * | 5/2002 | Roe | A61F 13/42 604/358 |
| 7,977,529 | B2 * | 7/2011 | Bergman | A61F 13/42 604/361 |
| 8,672,842 | B2 * | 3/2014 | Kenalty | A61B 5/0015 324/691 |
| 10,022,277 | B2 * | 7/2018 | Heil | A61F 13/42 |
| 2004/0127874 | A1 * | 7/2004 | Nishizawa | A61F 13/15699 604/385.01 |
| 2004/0220538 | A1 * | 11/2004 | Panopoulos | A61F 13/42 604/361 |
| 2004/0254549 | A1 * | 12/2004 | Olson | A61F 13/42 604/361 |
| 2005/0195085 | A1 * | 9/2005 | Cretu-Petra | A61B 5/6808 340/573.5 |
| 2006/0069360 | A1 * | 3/2006 | Long | A61F 13/42 604/361 |
| 2007/0142799 | A1 * | 6/2007 | Ales | A61F 13/42 604/361 |
| 2007/0270774 | A1 * | 11/2007 | Bergman | A61F 13/42 604/361 |
| 2008/0094226 | A1 * | 4/2008 | O'Shea | A61B 5/0002 340/573.1 |
| 2010/0152688 | A1 * | 6/2010 | Handwerker | A61F 13/42 604/361 |
| 2012/0150134 | A1 * | 6/2012 | Wei | A61L 15/56 604/361 |
| 2012/0271259 | A1 * | 10/2012 | Ulert | A61F 5/48 604/327 |
| 2012/0277637 | A1 * | 11/2012 | Vahdatpour | A47C 31/123 600/595 |
| 2013/0019405 | A1 * | 1/2013 | Flanagan | A61G 7/057 5/600 |
| 2013/0066289 | A1 * | 3/2013 | Song | A61L 15/56 604/361 |
| 2013/0296739 | A1 * | 11/2013 | Schultz | A61B 10/007 600/573 |
| 2014/0039351 | A1 * | 2/2014 | Mix | A61B 5/1114 600/587 |
| 2014/0121473 | A1 * | 5/2014 | Banet | A61B 5/6808 600/301 |
| 2014/0200538 | A1 * | 7/2014 | Euliano | A61F 13/42 604/361 |
| 2014/0221876 | A1 | 8/2014 | Eddy | |
| 2015/0042489 | A1 * | 2/2015 | LaVon | A61F 13/42 340/870.11 |
| 2015/0045630 | A1 * | 2/2015 | Poliakine-Baruchi | A61B 5/6892 600/301 |
| 2015/0157512 | A1 * | 6/2015 | Abir | A61F 13/42 340/573.5 |
| 2016/0008206 | A1 * | 1/2016 | Devanaboyina | A47C 9/002 601/136 |
| 2016/0166438 | A1 * | 6/2016 | Rovaniemi | A61F 13/00059 600/301 |
| 2017/0035622 | A1 * | 2/2017 | Wang | A61F 13/42 |

* cited by examiner

Section A-A

PATIENT MOVEMENT AND INCONTINENCE NOTIFICATION DEVICES

CROSS-REFERENCE TO RELATED APPLICATION

This application claims priority to U.S. Provisional Application No. 62/296,201 filed Feb. 17, 2016, entitled "PATIENT MOVEMENT AND INCONTINANCE NOTIFICATION DEVICES," the entire disclosure of which is hereby incorporated by reference herein.

BACKGROUND OF THE INVENTION

The present invention generally relates to a patient movement notification device, an incontinence notification device, a diaper with an incontinence notification device, a combined patient movement and incontinence notification device, a combined chuck and incontinence notification device, and a combined chuck, incontinence notification device, and patient movement notification device.

Patient movement notification devices serve to notify a patient's caretaker(s) who may better assist them. Such devices are used for patients who are at a high risk for fall-related injury or for patients who are not healthy enough to stand (post-operative patients, etc.).

Patient movement notification devices are currently in use that include a disposable sensor that is positioned between the patient and a bed, chair, or toilet, and an electronics module that connects to the sensor for generating an alarm when the patient removes pressure from the pad by getting out of bed or up from a chair. The alarm may be a recorded vocal command, such as "please stay in bed and use the nurse call button if you need assistance" or any other message that the caretaker may wish to record.

Existing patient movement notification devices suffer from several drawbacks. First, they may tend to give false alarms when the patient merely rolls over in bed. Second, they may not operate accurately when used on an air mattress, particularly for patients weighing between about 70 and 150 pounds because the sensor pads do not effectively discriminate between a loss of pressure from above or below the sensor pad. The sensors are considered to be disposable and are typically only to be used for 15 days or less because the sensors are pressure sensitive, and after having pressure continuously applied to the sensor, the sensor may not be able to re-expand when the patient removes pressure. However, hospitals have difficulty monitoring the times of use such that the sensors are often used well beyond the permitted 15-day lifetime.

Incontinence notification devices are known that are intended to detect when a patient has urinated in their bed. Such incontinence devices are placed under the patient's groin area and trigger an alarm upon sensing moisture, often by using conductive traces provided on the upper surface of a moisture-impermeable strip. The moisture-impermeable strips of such incontinence notification devices are disposable and do not serve to absorb urine.

Incontinence issues are often alternatively dealt with by using a "chuck," which is a large disposable absorbent pad placed under the patient. Such chucks are made of absorbent materials similar to those used in diapers. An example of such a chuck is disclosed in U.S. Pat. No. 6,675,702. Such chucks do not serve to notify a caregiver when a patient has urinated.

SUMMARY OF THE INVENTION

According to an embodiment of the present invention, a patient movement notification device is provided comprising: a sensor pad comprising a first sensing zone and a second sensing zone, the first sensing zone senses pressure applied by the patient to the first sensing zone and generates a first pressure signal upon a sensing pressure applied by the patient to the first sensing zone, the second sensing zone senses pressure applied by the patient to the second sensing zone and generates a second pressure signal upon a sensing pressure applied by the patient to the second sensing zone; and an electronics module communicatively coupled to the sensor pad for generating a notification of patient movement in response to receipt or non-receipt of at least one of the first pressure signal and second pressure signal from the sensor pad.

According to another embodiment of the present invention, a sensor pad is provided for use in a patient movement notification device. The sensor pad comprises: a first sensing zone and a second sensing zone, the first sensing zone senses pressure applied by the patient to the first sensing zone and generates a first pressure signal upon a sensing pressure applied by the patient to the first sensing zone, the second sensing zone senses pressure applied by the patient to the second sensing zone and generates a second pressure signal upon a sensing pressure applied by the patient to the second sensing zone.

According to another embodiment of the present invention, a notification device is provided for providing both patient movement notification and incontinence notification. The notification device comprises: a sensor pad comprising a pressure sensor for sensing pressure applied by a patient and generating a pressure signal upon a sensing pressure applied by the patient, the sensor pad further comprises first and second contiguous conductive tracings provided on an upper outer surface thereof for sensing moisture due to incontinence and generating a moisture detection signal when moisture spans the first and second conductive tracings; and an electronics module communicatively coupled to the sensor pad for generating a notification of patient movement in response to receipt of the pressure signal from the sensor pad, and for generating a notification of incontinence in response to receipt of the moisture detection signal from the sensor pad.

According to another embodiment of the present invention, a sensor pad is provided for providing both patient movement notification and incontinence notification. The sensor pad comprises: a pressure sensor for sensing pressure applied by a patient and generating a pressure signal upon a sensing pressure applied by the patient, the sensor pad further comprises first and second contiguous conductive tracings provided on an upper outer surface thereof for sensing moisture due to incontinence and generating a moisture detection signal when moisture spans the first and second conductive tracings.

According to another embodiment of the present invention, an incontinence notification device is provided comprising: a sensor pad comprising first and second contiguous conductive tracings provided on an upper outer surface thereof for sensing moisture due to incontinence and generating a moisture detection signal when moisture spans the first and second conductive tracings; an absorbent chuck comprising a moisture-impermeable sheet with an absorbent material on an upper surface thereof, wherein the moisture-impermeable sheet of the chuck has an aperture for receiving the sensor pad such that the first and second conductive tracings on the sensor pad are exposed through or above the aperture; and an electronics module communicatively coupled to the sensor pad for generating a notification of incontinence in response to receipt of the moisture detection signal from the sensor pad.

According to another embodiment of the present invention, an absorbent sensing pad is provided for use with an incontinence notification device. The absorbent sensing pad comprises: a sensor pad comprising first and second contiguous conductive tracings provided on an upper outer surface thereof for sensing moisture due to incontinence and generating a moisture detection signal when moisture spans the first and second conductive tracings; and an absorbent chuck comprising a moisture-impermeable sheet with an absorbent material on an upper surface thereof, wherein the moisture-impermeable sheet of the chuck has an aperture for receiving the sensor pad such that the first and second conductive tracings on the sensor pad are exposed through or above the aperture.

According to another embodiment of the present invention, a notification device is provided for providing both patient movement notification and incontinence notification. The notification device comprises: a sensor pad comprising a pressure sensor for sensing pressure applied by a patient and generating a pressure signal upon a sensing pressure applied by the patient, the sensor pad further comprising first and second contiguous conductive tracings provided on an upper outer surface thereof for sensing moisture due to incontinence and generating a moisture detection signal when moisture spans the first and second conductive tracings; an absorbent chuck comprising a moisture-impermeable sheet with an absorbent material on an upper surface thereof, wherein the moisture-impermeable sheet of the chuck has an aperture for receiving the sensor pad such that the first and second conductive tracings on the sensor pad are exposed through or above the aperture; and an electronics module communicatively coupled to the sensor pad for generating a notification of patient movement in response to receipt of the pressure signal from the sensor pad, and for generating a notification of incontinence in response to receipt of the moisture detection signal from the sensor pad.

According to another embodiment of the present invention, an absorbent sensor pad is provided for use in a notification device for providing both patient movement notification and incontinence notification. The absorbent sensor pad comprises: a sensor pad comprising a pressure sensor for sensing pressure applied by a patient and generating a pressure signal upon a sensing pressure applied by the patient, the sensor pad further comprising first and second contiguous conductive tracings provided on an upper outer surface thereof for sensing moisture due to incontinence and generating a moisture detection signal when moisture spans the first and second conductive tracings; and an absorbent chuck comprising a moisture-impermeable sheet with an absorbent material on an upper surface thereof, wherein the moisture-impermeable sheet of the chuck has an aperture for receiving the sensor pad such that the first and second conductive tracings on the sensor pad are exposed through or above the aperture.

According to another embodiment of the present invention, a sensor pad is provided for use in a patient movement notification device. The sensor pad comprises: a central region; a first depending leg extending from the central region in a first direction; a second depending leg extending from the central region in a second direction, which is opposite the first direction; a third depending leg extending from the central region in a third direction, which is substantially perpendicular to the first and second directions; a fourth depending leg extending from the central region in a fourth direction, which is opposite the third direction and substantially perpendicular to the first and second directions; and a pressure sensor for sensing pressure applied by a patient and generating a pressure signal upon a sensing pressure applied by the patient.

According to another embodiment of the present invention, a diaper is provided comprising: a sensor pad comprising first and second contiguous conductive tracings provided on an upper outer surface thereof for sensing moisture due to incontinence and generating a moisture detection signal when moisture spans the first and second conductive tracings; and a moisture-impermeable sheet with an absorbent material on an upper surface thereof, wherein the moisture-impermeable sheet has an aperture for receiving the sensor pad such that the first and second conductive tracings on the sensor pad are exposed through or above the aperture.

According to another embodiment of the present invention, a notification device is provided for providing patient movement notification and incontinence notification. The device comprises: a mattress having an integrated pressure sensor for sensing pressure applied by a patient and generating a pressure signal upon a sensing pressure applied by the patient; a sensor pad comprising first and second contiguous conductive tracings provided on an upper outer surface thereof for sensing moisture due to incontinence and generating a moisture detection signal when moisture spans the first and second conductive tracings; and an electronics module communicatively coupled to the pressure sensor for generating a notification of patient movement in response to receipt of the pressure signal from the pressure sensor, the electronics module communicatively coupled to the sensor pad for generating a notification of incontinence in response to receipt of the moisture detection signal from the sensor pad.

These and other features, advantages, and objects of the present invention will be further understood and appreciated by those skilled in the art by reference to the following specification, claims, and appended drawings.

DETAILED DESCRIPTION OF PREFERRED EMBODIMENTS

Figure 1:
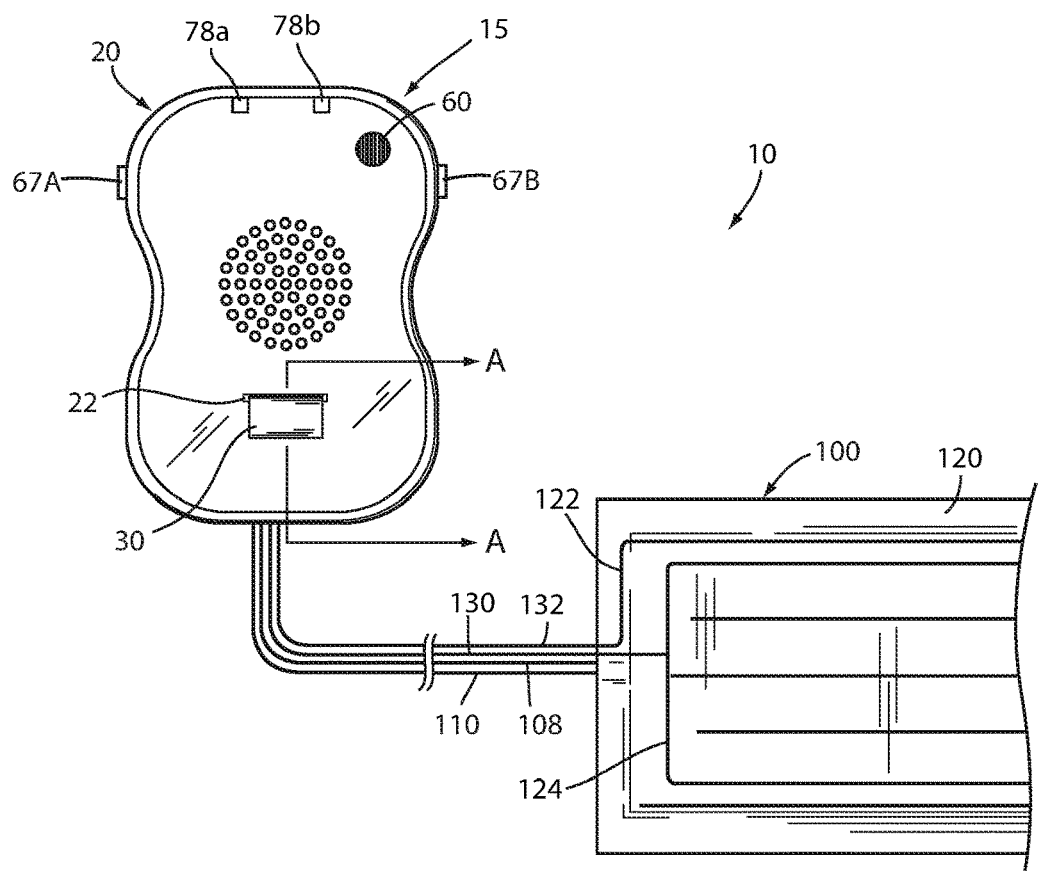
FIG. 1 is a partial isometric view of a patient movement notification device according to an embodiment of the present invention.

Reference will now be made in detail to the present preferred embodiments of the invention, examples of which are illustrated in the accompanying drawings. Wherever possible, the same reference numerals will be used throughout the drawings to refer to the same or like parts. In the drawings, the depicted structural elements are not to scale and certain components are enlarged relative to the other components for purposes of emphasis and understanding.

Various embodiments of a notification device are described herein. In some embodiments, the notification device issues a notification upon detection of patient movement. In other embodiments, the notification device issues a notification upon detection of patient incontinence. In still other embodiments, the notification device issues notifications upon detection of patient movement and/or patient incontinence. In each embodiment, the notification device 10 includes a sensor pad 100 and an electronics module 15. The configurations of the sensor pad 100 and electronics module 15 may vary from embodiment to embodiment.

Figure 1A:
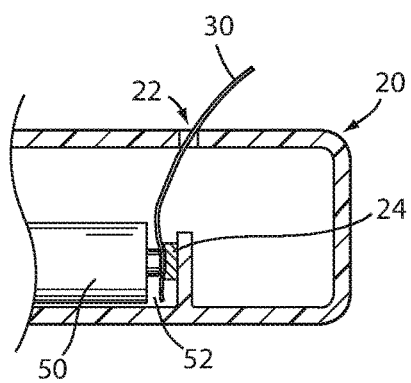
FIG. 1A is an elevational view of a cross section of a portion of the electronics module of the patient movement notification device shown in FIG. 1 taken along line A-A.
Figure 2:
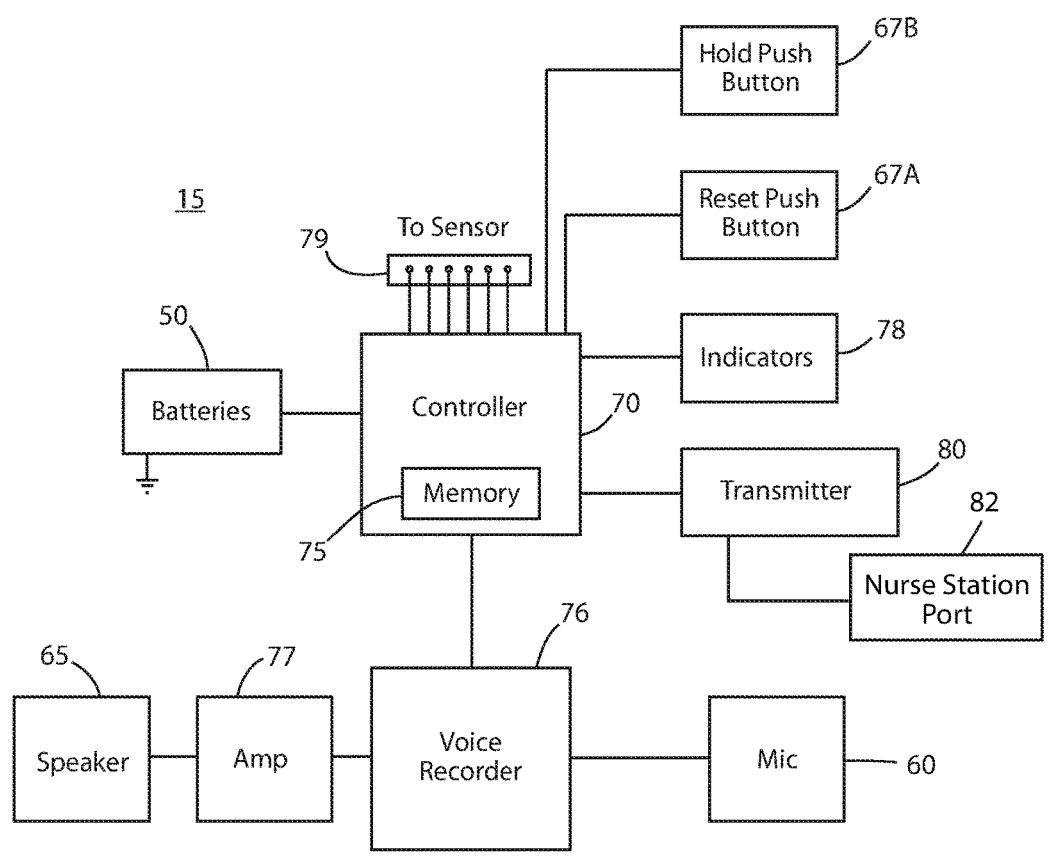
FIG. 2 is an electrical circuit diagram in block form of the electronics module of the patient movement notification device shown in FIG. 1.

The electronics module 15 may be configured as shown in FIG. 1 to include a housing 20 that contains the electronics (described below) and at least one battery 50 (FIGS. 1A and 2). The electronics that may be included in housing 20 are shown in FIG. 2. As shown, the electronics module 15 includes a connector 79 that may be a connector receptacle to receive a plug end of a wire extending from a sensor pad 100 or may be a permanent connection to the sensor pad. The electronics may take any form capable of storing a voice recording and playing the voice recording back upon determining that the patient is moving in response to a signal from the sensor pad 100. As such, the electronics include a microphone 60, a speaker 65, a RESET push button 67A, a HOLD push button 67B, a controller 70 (which may be a microprocessor, digital signal processor, or discrete electronic components), memory 75 (which may be memory internal to a microprocessor), a voice recorder 76, an audio amplifier 77, connector 79 for connecting to the sensor pad 100, and one or more batteries 50. In lieu of connector 79, the sensor pad 100 may be hardwired to electronics module 15, particularly if the electronics module is disposable so as to be disposed of with the sensor pad. The electronics may further include LED indicators 78a and 78b (FIG. 1), and a transmitter/receiver 80 as further described below.

Optional transmitter 80 may be provided to transmit information (which may include alarms and other data) to a distant receiver that receives the information. This information may then be stored in an automated records database of the healthcare facility or otherwise at a nurses' station. The information may include any one or more of the following: warnings that a patient has wet their bed; warnings of a patient getting out of bed, out of a chair or wheelchair, or off of a toilet; the time and date of issuance of the warnings and the time and date the patient returned to bed or the chair; warnings of sensor pad end of life approaching with a time and date stamp; and warning of sensor pad end of life with a time and date stamp. The time and date stamps may be generated at the receiving side of the information and stored in the records database. Transmitter 80 may be coupled wirelessly or by a wired connection such as a USB. The records database may be a database such as a Cerner or EPIC records database.

Transmitter 80 may be coupled wirelessly or by wired connection to a nursing station alarm switchboard so as to generate appropriate alarm signals at a nursing station that identify the patient or room and the warnings so that the staff can take appropriate action. A connection port 82 may be provided for a wired connection to the nursing station.

Controller 70 may also store historical information in memory 75 (or otherwise transmit the necessary information to the nursing station and/or records database so that the historical information may be stored). Such historical information may include times of day that the patient historically suffers from incontinence and/or gets out of bed or attempts to get out of bed. By tracking this historical information, nurses may be sent a warning via cell phone text or other alarm mechanism to check on the patient just prior to those historical times so as to avoid the incontinence event altogether.

In some facilities, video monitoring may be used to identify when a patient has or is about to get out of bed. While this technique can be effective, there are often too many monitors for one person to watch. By using the alarm system of the present invention, a nurse or other person watching the video monitors may be warned to view a particular patient, when, for example, the fall prevention alarm is triggered. If the patient has or is attempting to get out of bed, a nurse may be sent to that room. However, if the patient has merely moved in bed so as to trigger the fall prevention alarm, the person watching the monitors may see that a nurse does not need to respond and simply reset the alarm remotely. This cuts down on false notifications that would otherwise consume significant time of the nursing staff.

According to a first embodiment, notification device 10 is configured for providing patient movement notification and incontinence notification. Accordingly, notification device 10 includes a sensor pad 100 having a pressure sensor 111 (FIGS. 3 and 8) for sensing pressure applied by a patient and generating a pressure signal upon a sensing pressure applied by the patient, also having a first contiguous conductive tracing 122 and a second contiguous conductive tracing 124 provided on an upper outer surface 120 thereof for sensing moisture due to incontinence and generating a moisture detection signal when moisture spans first and second conductive tracings 122 and 124. In this first embodiment, electronics module 15 is communicatively coupled to sensor pad 100 for generating a notification of patient movement in response to receipt of the pressure signal from sensor pad 100, and for generating a notification of incontinence in response to receipt of the moisture detection signal from sensor pad 100. By providing both patient movement notification and incontinence notification with the same notification device 10, only one sensor pad 100 and one electronics module 15 need be provided to perform both notification functions that previously required two separate sensor pads and two separate electronics modules.

Figure 3:
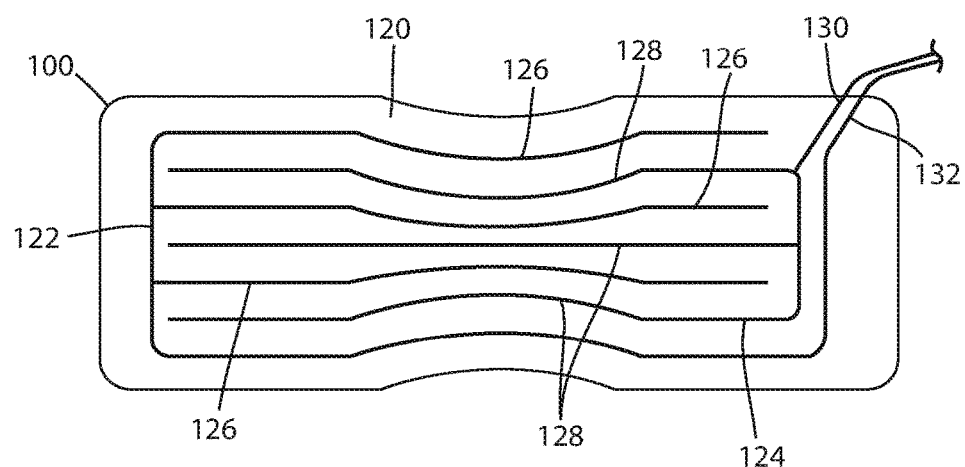
FIG. 3 is a top plan view of a sensor pad according to a first embodiment.

Sensor pad 100 may be constructed as shown in FIGS. 1 and 3. In general, sensor pad 100 may be constructed in any manner so as to provide a pressure sensor that senses pressure applied by a patient and generates a pressure signal upon a sensing pressure applied by the patient. Specific constructions of this aspect of the sensor pad 100 are described further below. In order to have sensor pad 100 function as an incontinence sensor, first contiguous conductive tracing 122 and second contiguous conductive tracing 124 are disposed on an upper surface 120 of sensor pad 100. Each of the first and second contiguous conductive tracings may be printed on the surface of sensor pad 100 using an electrically conductive ink in a pattern that maintains spacing between respective interdigitated branches 126 and 128 of first and second contiguous conductive tracings 122 and 124. A wire 130 connects first contiguous conductive tracing 122 to controller 70 of electronics module 15, and another wire 132 connects second contiguous conductive tracing 124 to either controller 70 or a fixed voltage reference. The interdigitated branches 126 and 128 of first and second contiguous conductive tracings 122 and 124 are spaced far enough apart that controller 70 detects an open circuit when sensor pad 100 is dry. However, when urine is present on upper surface 120 of sensor pad 100, the urine spans across the interdigitated branches 126 and 128 of first and second contiguous conductive tracings 122 and 124 and thereby creates a path of electrical conductivity between first and second contiguous conductive tracings 122 and 124 such that controller 70 senses a closed circuit. Upon sensing such a closed circuit, controller 70 may generate an alarm and/or call to the nurses' station, which may be sent via the existing nurse call system in the hospital. Electronics module 15 may be configured such that the incontinence alarm or call would continue until the sensor pad 100 is replaced with a new dry sensor pad.

As used herein, the term "communicatively coupled" means that two components are associated and configured so that they communicate with one another. Such communicative coupling may be provided by hardwiring the devices or by providing for wireless communication therebetween. Thus, the sensor pad 100 may further include a transmitter and/or a receiver for sending/receiving wireless signals to/from electronics module 15.

Figure 4:
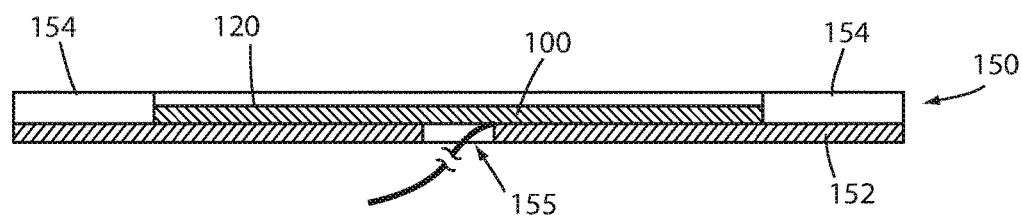
FIG. 4 is a cross-sectional view of a first version of an absorbent sensor pad according to a second embodiment.
Figure 5:
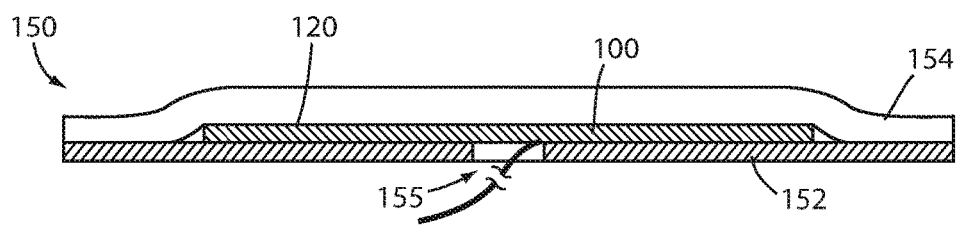
FIG. 5 is a cross-sectional view of a second version of an absorbent sensor pad according to a second embodiment.

In accordance with a second embodiment, a notification device 10 as described above in the first embodiment is used in combination with an absorbent chuck 150 as shown in FIGS. 4 and 5. Absorbent chuck 150 includes a moisture-impermeable sheet 152 (such as a plastic sheet) with an absorbent material 154 on an upper surface thereof. Moisture-impermeable sheet 152 of absorbent chuck 150 has an aperture 155 for receiving sensor pad 100 such that first and second conductive tracings 122 and 124 on sensor pad 100 are exposed through or above aperture 155. Absorbent material 154 may extend over upper surface 120 of sensor pad 100 (FIG. 5) or may be removed from that region above sensor pad 100 (FIG. 4). By providing absorbent chuck 150 on/around sensor pad 100, urine may be absorbed by chuck 150 in a conventional manner to keep the bedding dry. Previously, the use of an absorbent chuck would make it difficult to use an incontinence sensor pad due to the presence of the moisture-impermeable sheet 152 which would otherwise block the urine from reaching the sensor pad. Aside from being modified to include aperture 155 to accommodate sensor pad 100, absorbent chuck 150 may be constructed in any conventional manner.

Although this embodiment is described as using the sensor pad 100 of the first embodiment, it should be appreciated that sensor pads according to the other embodiments described herein may be used with absorbent chuck 150. Further, a sensor pad may be used with the absorbent chuck that only senses incontinence and that does not also sense patient movement.

Figure 6:
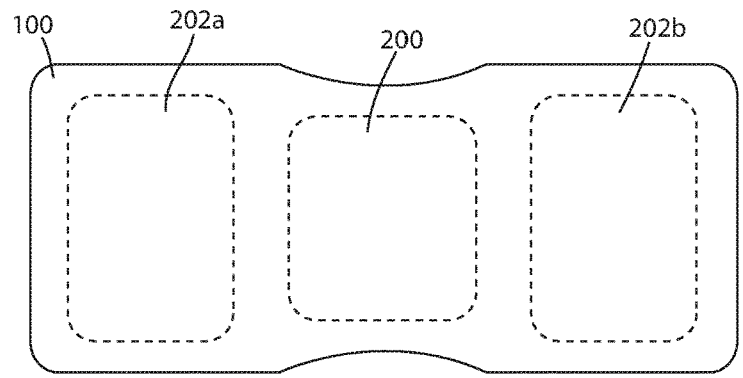
FIG. 6 is a top plan view of a sensor pad according to a third embodiment.

FIG. 6 shows an example of a third embodiment of a notification device 10. In this third embodiment, sensor pad 100 is configured to include a first sensing zone 200 and a second sensing zone 202a. First sensing zone 200 senses pressure applied by the patient to the first sensing zone and generates a first signal upon a sensing pressure applied by the patient to the first sensing zone 200. Second sensing zone 202a senses pressure applied by the patient to the second sensing zone 202a and generates a second signal upon a sensing pressure applied by the patient to the second sensing zone 202a. Electronics module 15 generates a notification of patient movement in response to receipt or non-receipt of at least one of the first signal and second signal from sensor pad 100 in the manner described below. As described below, a third sensing zone 202b may optionally be provided that senses pressure applied by the patient to the third sensing zone 202b. Additional sensing zones may also be provided.

As discussed above, existing patient movement notification devices may tend to give false alarms when the patient merely rolls over in bed. By providing at least the two separate sensing zones 200 and 200a, a multi-zone sensor pad 100 may be provided that more accurately determines when a patient has moved off the bed or is about to move off the bed while significantly reducing false alarms. This is accomplished by providing a multi-zone sensing pad 100 that provides additional information to electronics module 15 such that controller 70 may make a more accurate determination as to patient movement. The manner in which controller 70 uses the information from the various zones is described further below.

First sensing zone 200 is located on sensor pad 100 such that it will be disposed at the center of the bed where the patient is most likely to lie. Second sensing zone 202a is located on sensor pad 100 towards a side of the bed where the patient may exit the bed. If the optional third sensor zone 202b is provided, third sensing zone 202b is located on sensor pad 100 on an end of the sensor pad opposite an end where second sensing zone 202a is located so as to be positioned toward an opposite side of the bed where the patient may exit the bed. As will be apparent, a sensor pad 100 with a third sensing zone 202b would most likely be used when a patent's bed is positioned to allow the patient to exit either side of the bed. If the bed is against a wall so that there is only one side from which the patient may exit the bed, a two-zone sensor pad would be sufficient.

When used with a multi-zone sensing pad 100, electronics module 15 may be configured to enter a monitoring mode upon receipt of the first signal generated from centrally located first sensing zone 200. Thus, receipt of the first signal indicates that the patient is applying pressure to first sensing zone 200 and that the patient is now in bed. When in the monitoring mode, electronics module 15 does not generate a notification of patient movement so long as the first signal is received. Note that the first signal need not be continuously received as controller 70 may sample the output from sensor pad 100 at periodic intervals to conserve battery power. When in the monitoring mode, electronics module 15 generates a notification of patient movement when either (1) the first signal has not been received for a predetermined time period (of, for example, two seconds) and no signal is received from second sensing zone 202a (or third sensing zone 202b if present), or (2) the first signal is no longer being received but the second signal (or third signal if sensor pad 100 has a third sensing zone) is received thereby indicating that the patient has moved from first sensing zone 200 to second sensing zone 202a (or the optional third sensing zone 202b) and is in the process of exiting the bed. By waiting for the predetermined time period in the event that the first signal has not been received but no signal has been received from either the second or third sensing zones, false alarms are prevented in the event the patient has simply lifted up off the first sensing zone 200 while rolling over. However, if the predetermined time period passes, electronics module 15 generates a notification of patient movement because it becomes likely that the patient has attempted to exit the bed from an end of the bed rather than a side of the bed as would have otherwise been detected by the second or third sensor zones 202a and 202b.

The notification of patient movement generated by electronics module 15 may include an audio and/or visual alarm and/or a call to the nurses' station, which may be sent via the existing nurse call system in the hospital. The audio alarm may include playback of a prerecorded message such as "Please remain in your bed." Different messages may be played back depending upon the signals received from the various sensing zones. For example, if a first signal is no longer received from first sensing zone 200, but a signal is received from second sensing zone 202a (or third sensing zone 202b), controller 70 determines that the patient has not yet left the bed, but is about to leave the bed, and may play back a message such as "Please remain in your bed. If you need assistance please use the nurse call button." In this event, the nurses' station may or may not be called. However, if no signals are received from either the first or second sensing zones (or the third sensing zone) for the predetermined time period, controller 70 determines that the patient has left the bed, and may play back a message such as "Please return to your bed. A nurse has been called." In this event, the nurses' station may be called. Thus, not only may different messages be played back depending upon the conditions, but calls to the nurses' station may be dependent upon the conditions sensed using multiple sensing zones.

Although the notification device 10 according to the third embodiment is only described above as a patient movement notification device, conductive tracings similar to those in the first embodiment may be provided on the upper surface of sensor pad 100 such that the notification device may also function as an incontinence notification device. Further, an absorbent chuck 150 may be combined with sensor pad 100 in the same manner as discussed above with respect to the second embodiment.

Figure 7:
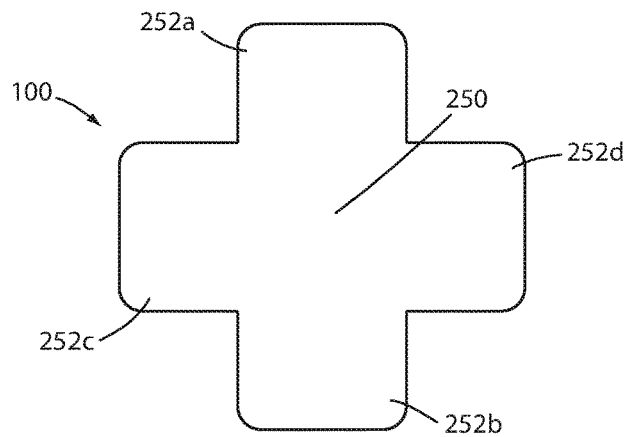
FIG. 7 is top plan view of a sensor pad according to a fourth embodiment.

As mentioned above, another problem associated with patient movement notification devices is that they may not operate accurately when used on an air mattress, particularly for patients weighing between about 70 and 150 pounds because the sensor pads do not effectively discriminate between a loss of pressure from above or below the sensor pad. To address this problem, a fourth embodiment of a notification device 10 includes a modified sensor pad 100 (FIG. 7) that includes a central region 250 and four depending legs 252a-252d. A first depending leg 252a extends from central region 250 in a first direction and a second depending leg 252b extends from central region 250 in a second direction, which is opposite the first direction. A third depending leg 252c extends from central region 250 in a third direction, which is substantially perpendicular to the first and second directions. A fourth depending leg 252d extends from central region 250 in a fourth direction, which is opposite the third direction and substantially perpendicular to the first and second directions. By providing the depending legs 252a-252d, the effective area of sensor pad 100 may be increased without simply increasing the size of a conventionally-shaped sensor pad and thereby without also proportionally increasing the material cost of the sensor pad.

Although the notification device 10 according to the fourth embodiment is only described above as a patient movement notification device, conductive tracings similar to those in the first embodiment may be provided on the upper surface of sensor pad 100 such that the notification device 10 may also function as an incontinence notification device. Further, an absorbent chuck 150 may be combined with sensor pad 100 in the same manner as discussed above with respect to the second embodiment. In addition, sensor pad 100 may include multiple sensing zones as described in the third embodiment.

For each of the embodiments described above, the sensor pad 100 is disposable and would therefore be sold separately and configured to be removably communicatively coupled to electronics module 15. Accordingly, for the four above embodiments, there are four additional embodiments constituting just the respective sensor pads, which may be used in combination with the absorbent chuck 150.

The electronics module 15 may be reusable or may be disposable as described in U.S. Patent Application Publication No. US 2014/0221876 A1, the entire disclosure of which is incorporated herein by reference.

The benefit of making electronics module 15 disposable is that it eliminates the need for monitoring this portion of the notification device as a capital asset. In addition, the electronics module may be constructed to permanently shut itself down to become non-functional a specified number of days after activation (i.e., 15 days from activation). In this way, the hospital can replace the sensors every 15 days as recommended by only checking if the device has shut down or is about to shut down rather than logging the dates of first use. In this regard the electronics module may give an advance warning a few hours in advance and then shuts down. Because the device may be designed to relay the warning signal of patient movement to a nursing station, the device may further transmit the advance warning of shutdown to the nursing station as well. It should be appreciated that the shutdown (or time out) feature may be modified for non-disposable modules so that it provides a warning that the 15-day period is over or almost over.

In the event that the electronics module is designed to be disposable, housing 20 (FIGS. 1 and 1A) may be designed so that it does not allow access to the battery 50 such that it cannot be replaced or removed. This reduces parts count and cost of the unit and provides an inexpensive mechanism for activating the device as described further. Housing 20 further may include a slot 22 positioned proximate one end 52 of the battery 50 and a battery terminal 24 to which that end 52 of battery 50 connects as shown in partial cross section in FIG. 1A. A plastic tab 30 is provided that extends from housing 20 through slot 22 and between end 52 of battery 50 and terminal 24 so as to prevent the electronics from receiving power until such time as a user pulls the tab 30 from slot 22.

Figure 8:
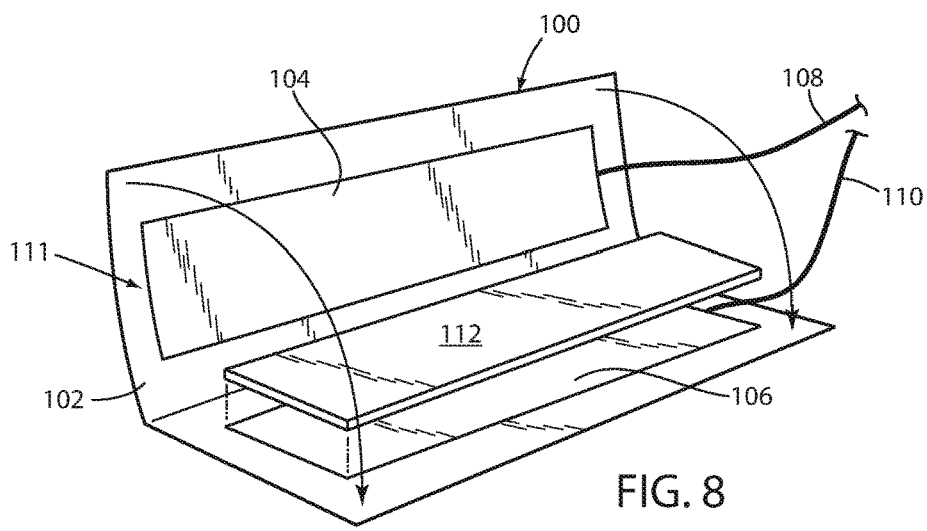
FIG. 8 is a perspective view of a sensor pad of the patient movement notification device shown in FIG. 1 shown in a partially assembled state.

The pressure sensor of sensor pad 100 may have a conventional construction or may have the construction shown in FIG. 8. Conventional pressure sensors are constructed using three pieces of cardboard, two of which are coated with conductive pads facing one another and a third piece of cardboard having foam attached thereto is placed in between the other two pieces of cardboard. A wire is attached to each conductive pad and then the sensor is sealed within a plastic pouch.

FIG. 8 shows an example of a pressure sensor 111 for sensor pad 100 whereby the inside surfaces of a sheet 102 (such as a plastic sheet) have conductive ink printed thereon to form conductive contacts 104 and 106. Wires 108 and 110 may then be secured to the conductive contacts and foam 112 may then be laid over one of the conductive contacts. The sheet 102 may then be folded and sealed such that the conductive contacts 104 and 106 face one another with foam 112 disposed therebetween. Such a sensor 100 may be formed in many different sizes and shapes. The novel sensor thus has fewer parts and lower cost. The sensor 100 shown in FIG. 8 is disclosed in commonly assigned U.S. Patent Application Publication No. US 2014/0221876 A1, the entire disclosure of which is incorporated herein by reference. A sensor pad having either the conventional pressure sensor construction or the construction shown in FIG. 8, may be used in any of the above embodiments.

In addition to providing the sensor on a bed, chair or wheelchair, another version of the sensor may be placed on a toilet to notify a caretaker that the patient has attempted to get up from the toilet on their own. A sensor for such a toilet application may be constructed using a flexible circuit that may be connected and adhered to a surface of the toilet that will contact the patient's skin. The device would thus sense the properties of human skin, not pressure. The unit activates once the patient touches the flex circuit contacts. Alternatively, the toilet sensor may be configured to sense pressure and may be placed between the toilet seat and the toilet bowl or on top of the toilet seat.

A low cost microcontroller may be used as controller 70 and may serve multiple purposes including: application logic, generating an alarm tone, coordinating the actions of other components, and switch sensing. One suitable microcontroller is the PIC24F04KA200. It is an inexpensive entry level 16-bit controller in the PIC24 product catalogue from Microchip. This particular controller benefits from its low cost and small form factor. The microcontroller operates at low voltages, nominally 3.0V, but is capable of operating while the battery level drops over its operating life (2.8 V).

The controller 70 is responsible for coordinating the actions of the device. Specifically, if electronics module 15 is disposable, controller 70 tracks the time that the unit is active (measured from initial power up). This time is cumulative and is stored periodically in non-volatile memory 75 (preventing tampering). When a predetermined lifetime expires, controller 70 no longer provides its basic operating functions. This requires the user to replace the unit.

The controller 70 does not have to actually record any sound data; however, it may control the state and operation of a voice recorder. Given user input (from the button 67 or the patient sensor), the controller will command the voice recorder to record or play back. The voice recorder is solely responsible for handling the audio details.

Playback of a recording may also be performed by the voice recorder. The alarm tone that the unit may generate may be the controller's responsibility. This is done by simply toggling a pin that is connected to the audio line. This appears as a square wave to an audio amplifier, which in turn generates a loud alarm. The controller controls the power-up state of the audio amplifier. This is done to intelligently reduce power consumption during inactive periods. The controller turns the amplifier on only when required.

Lastly, the controller senses user input. The button 67B for recording is tracked by the controller. More importantly the controller contains all of the hardware for sensing patient contact with an attached flex circuit or patient sensor. The controller may be programmed through a PGM connector.

The outer surfaces of housing 20 and sensor pad 100 are preferably treated with an antimicrobial substance. The surfaces of housing 20 and sensor pad 100 are coated with an antimicrobial treatment that may be sprayed onto the surfaces using a solution and/or may be applied using wipes soaked in such a solution. Suitable wipes and solutions are disclosed in commonly assigned U.S. Pat. No. 8,491,922, the entire disclosure of which is incorporated herein by reference.

Figure 9A:
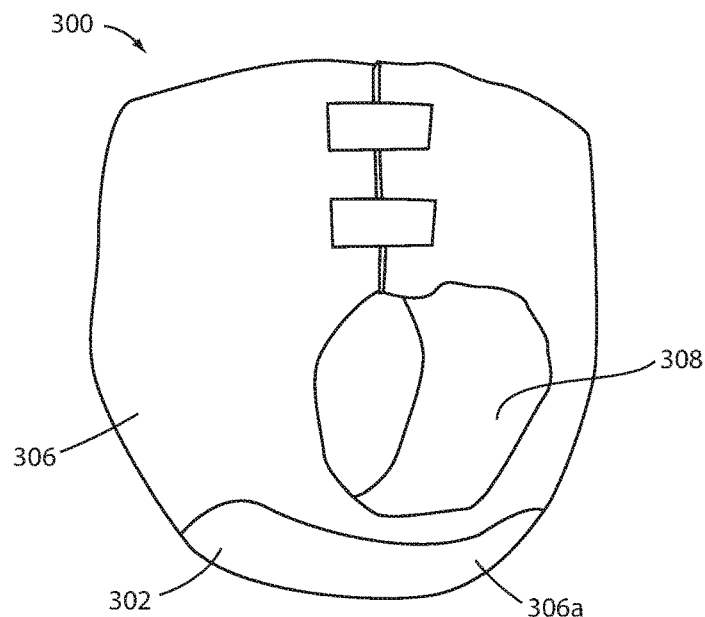
FIG. 9A is a perspective view of diaper having an incontinence sensing device.
Figure 9B:
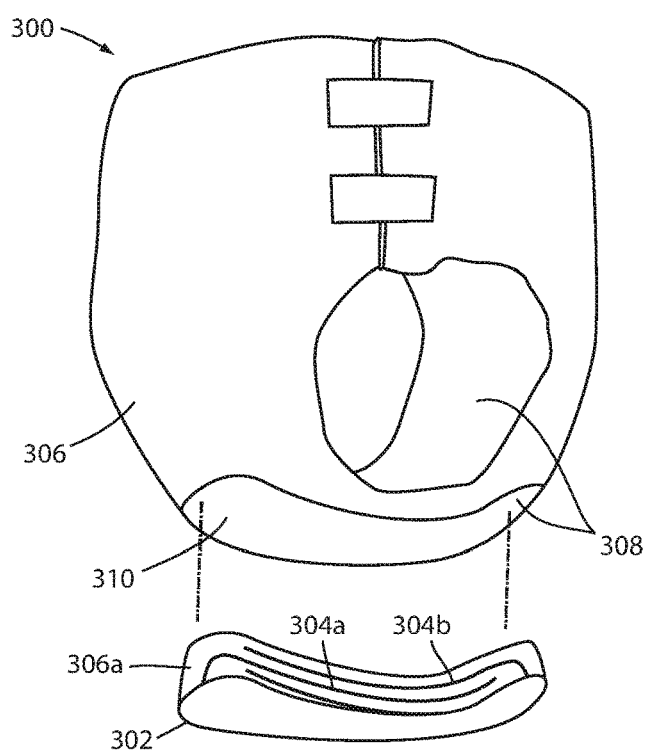
FIG. 9B is an exploded perspective view of a diaper having an incontinence sensing device.

FIGS. 9A and 9B show a diaper 300 having an integrated incontinence sensor pad 302 having a moisture-impermeable sheet 306a with a first contiguous conductive tracing 304a and a second contiguous conductive tracing 304b both provided on an upper inner surface thereof for sensing moisture due to incontinence and generating a moisture detection signal when moisture spans the first and second conductive tracings 304a and 304b. Diaper 300 further includes a moisture-impermeable sheet 306 with an absorbent material 308 on an upper inner surface thereof. Moisture-impermeable sheet 306 has an aperture 310 for receiving sensor pad 302 such that first and second conductive tracings 304a and 304b on sensor pad 302 are exposed through or above aperture 310. Moisture-impermeable sheet 306 and absorbent material 308 may be made of any conventional materials used in adult or baby diapers. The sensor pad 302 may include a transmitter for wirelessly transmitting the moisture detection signal to a notification device, which may be at a nurses' station.

Figure 10:
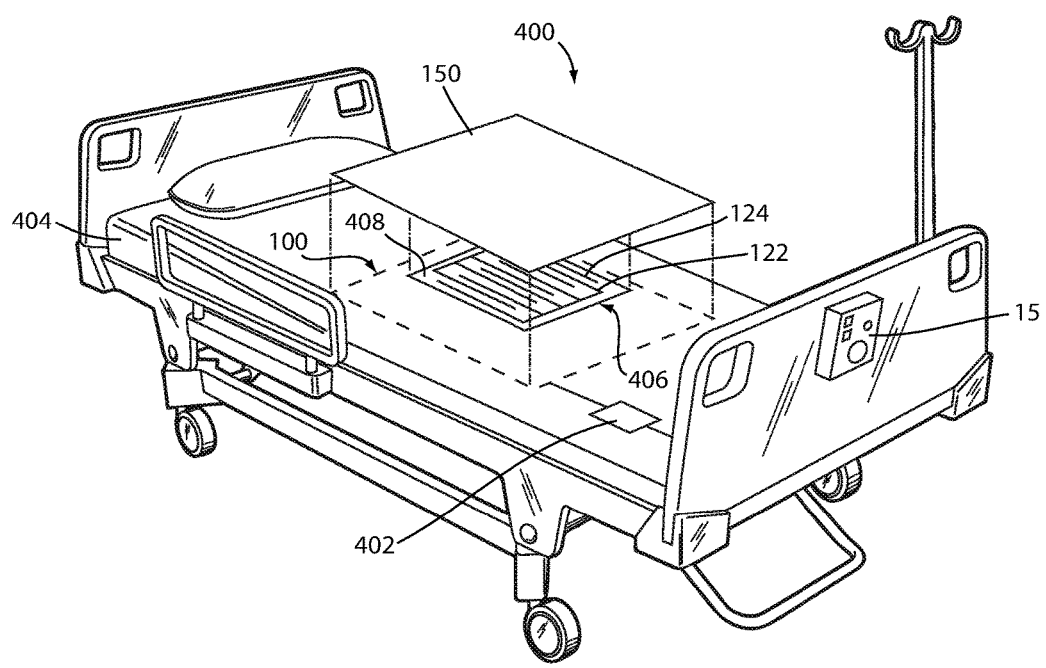
FIG. 10 is a perspective view of an absorbent chuck/incontinence sensing device and a bed with which the patient movement notification device may be integrated.

Various aspects of the above embodiments may be integrated into a bed. For example, the patient movement notification device sensor pad 100 may be integrated into a bed mattress. An example of such a bed 400 is shown in FIG. 10. In this case, the bed 400 may include an electronic interface 402 to connect the integrated sensor pad 100 to electronics module 15 via wired or wireless connection, and an absorbent chuck 150 and incontinence sensor 406 may be provided on top of the mattress 404 and may be connected to the electronic interface 402 included in the bed 400 so that a common electronics module 15 or alarm interface may be used. Incontinence sensor 406 may include a moisture impermeable sheet 408 with tracings 122 and 124 provided thereon.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by any subsequently presented claims as interpreted according to the principles of patent law, including the doctrine of equivalents.

What is claimed is:

1. A sensor pad for use in a notification device for providing patient movement notification and incontinence notification, said sensor pad comprising:
   a sheet;
   a pressure sensor for sensing pressure applied by a patient and generating a pressure signal upon a sensing pressure applied by the patient, the pressure sensor comprising conductive ink printed on a first surface of the sheet to form first and second conductive contacts, and a foam provided over one of said first and second conductive contacts;
   first and second contiguous conductive tracings provided on an upper outer surface of said sheet opposite the first surface on which said conductive ink is printed for sensing moisture due to incontinence and generating a moisture detection signal when moisture spans said first and second conductive tracings,
   wherein said sheet is folded and sealed such that said first and second conductive contacts are inside said sensor pad and face one another with said foam disposed therebetween to form said pressure sensor, and such that said first and second conductive tracings are located on the upper outer surface of said sensor pad.

2. The sensor pad of claim 1 and further comprising:
first and second wires each secured to a respective one of said first and second conductive contacts, wherein said first and second wires provide an electrical coupling to an electronics module of the notification device; and
third and fourth wires each secured to a respective one of said first and second conductive tracings, wherein said third and fourth wires provide an electrical coupling to the electronics module of the notification device.

3. The sensor pad of claim 1, and further comprising:
an absorbent chuck comprising a moisture-impermeable sheet with an absorbent material on an upper surface thereof,
wherein said moisture-impermeable sheet of said chuck having an aperture for receiving said sensor pad such that said first and second conductive tracings on said sensor pad are exposed through or above said aperture.

4. The sensor pad of claim 1, wherein said sensor pad comprises:
a central region;
a first depending leg extending from said central region in a first direction;
a second depending leg extending from said central region in a second direction, which is opposite the first direction;
a third depending leg extending from said central region in a third direction, which is substantially perpendicular to the first and second directions; and
a fourth depending leg extending from said central region in a fourth direction, which is opposite the third direction and substantially perpendicular to the first and second directions.

5. A notification device for providing patient movement notification and incontinence notification, the device comprising the sensor pad of claim 1 and an electronics module communicatively coupled to said sensor pad for generating a notification of patient movement in response to receipt of the pressure signal from said sensor pad, and for generating a notification of incontinence in response to receipt of the moisture detection signal from said sensor pad.

6. The notification device of claim 5, wherein the sensor pad comprises a first sensing zone and a second sensing zone, the first sensing zone senses pressure applied by the patient to the first sensing zone and generates a first pressure signal upon a sensing pressure applied by the patient to the first sensing zone, the second sensing zone senses pressure applied by the patient to the second sensing zone and generates a second pressure signal upon a sensing pressure applied by the patient to the second sensing zone, and wherein said electronics module generates a notification of patient movement in response to receipt or non-receipt of at least one of the first pressure signal and second pressure signal from said sensor pad.

7. The notification device of claim 6, wherein said first sensing zone is located on the sensor pad towards the center of a bed where the patient is most likely to lie, and wherein said second sensing zone is located on the sensor pad towards a side of the bed where the patient may exit the bed.

8. The notification device of claim 7, wherein said electronics module enters a monitoring mode upon receipt of the first pressure signal, wherein receipt of the first pressure signal indicates that the patient is applying pressure to the first sensing zone.

9. The notification device of claim 8, wherein, when in the monitoring mode, said electronics module does not generate a notification of patient movement so long as the first pressure signal is received.

10. The notification device of claim 8, wherein, when in the monitoring mode, said electronics module generates a notification of patient movement when the first pressure signal has not been received for a predetermined time period.

11. The notification device of claim 8, wherein, when in the monitoring mode, said electronics module generates a notification of patient movement when the first pressure signal is no longer being received but the second pressure signal is received thereby indicating that the patient has moved from the first sensing zone to the second sensing zone.

12. The notification device of claim 7, wherein said sensor pad comprises a third sensing zone that senses pressure applied by the patient to the third sensing zone and generates a third pressure signal upon a sensing pressure applied by the patient to the third sensing zone, wherein said third sensing zone is located on the sensor pad on an end of said sensor pad opposite an end where said second sensing zone is located so as to be positioned toward an opposite side of the bed where the patient may exit the bed.

13. The notification device of claim 12, wherein said electronics module enters a monitoring mode upon receipt of the first pressure signal, wherein receipt of the first pressure signal indicates that the patient is applying pressure to the first sensing zone.

14. The notification device of claim 13, wherein, when in the monitoring mode, said electronics module generates a notification of patient movement when the first pressure signal is no longer being received, but either the second pressure signal or the third pressure signal is received thereby indicating that the patient has moved from the first sensing zone to either the second sensing zone or the third sensing zone.

15. The notification device of claim 6, wherein said sensor pad is integrated into a mattress of a bed.

16. The sensor pad of claim 1, wherein the sheet is made of a moisture impervious material.

* * * * *